United States Patent [19]

Laughlin

[11] 4,287,174

[45] Sep. 1, 1981

[54] ANTI-ULCER COMPOSITION

[75] Inventor: Robert G. Laughlin, Cincinnati, Ohio

[73] Assignee: The Proctor & Gamble Company, Cincinnati, Ohio

[21] Appl. No.: 16,655

[22] Filed: Mar. 1, 1979

Related U.S. Application Data

[63] Continuation-in-part of Ser. No. 892,242, Mar. 31, 1978, abandoned.

[51] Int. Cl.³ .................... A61K 33/12; A61K 33/10; A61K 33/08; A61K 31/205
[52] U.S. Cl. .................................... 424/78; 424/127; 424/155; 424/156; 424/157; 424/180; 424/212; 424/233; 424/316
[58] Field of Search ................. 424/10, 311, 312, 316, 424/234, 233, 212, 127, 155, 156, 157, 180, 78

[56] References Cited

U.S. PATENT DOCUMENTS

| 3,092,474 | 6/1963 | Ebner | 44/66 |
| 3,459,795 | 8/1969 | Frank et al. | 260/526 |
| 4,046,899 | 9/1977 | Bodor | 424/250 |

FOREIGN PATENT DOCUMENTS 793473  1/1936  France ..................................... 424/316

Primary Examiner—Frederick E. Waddell
Attorney, Agent, or Firm—Jerry J. Yetter; Steven J. Goldstein; Jack D. Schaeffer

[57] ABSTRACT

Zwitterionic surfactant compounds provide effective therapy for ulceration of the gastric mucosa. The tendency of aspirin and other salicylate-based drugs to cause ulceration of the gastric mucosa is also reduced by administration of such drugs in conjunction with certain zwitterionic surfactants. The ammoniohexanoate zwitterionics are especially preferred in the management of both gastric and duodenal ulcers.

16 Claims, No Drawings

ANTI-ULCER COMPOSITION

This application is a continuation-in-part of previously filed application Ser. No. 892,242 filed Mar. 31, 1978 now abandoned.

TECHNICAL FIELD

The present invention relates to compositions and processes for preventing or relieving ulceration of the gastric mucosa. The invention also relates to salicylate compositions which safely relieve pain and inflammation. More specifically, certain zwitterionic surfactants have now been found to be effective in the management of "peptic" ulcers, including salicylate-induced ulcers. The zwitterionic surfactants disclosed herein can be administered alone to treat ulcers, or can be used in conjunction with salicylate-type drugs such as aspirin, and the like, to reduce or prevent the stomach irritation and/or ulceration often associated with the oral use of salicylate drugs.

Ulceration of any portion of the gastric mucosa is commonly referred to by the lay person as "an ulcer." Medically, ulcers are more precisely defined by their situs in the gastrointestinal tract. Thus, duodenal ulcers most commonly occur in the duodenal bulb. Gastric ulcers most commonly occur along the lesser curvature of the stomach. Ulcers can also form in the pyloric canal, in a position in the duodenum beyond the duodenal bulb, in the jejunum, etc. Such ulcers are referred to as channel ulcers, postbulbar ulcers, marginal or stomal ulcers, and jejunal ulcers. Etiologically, ulceration appears to be caused by a lack of balance between the ulcer-promoting factors, such as stomach acid and pepsin, and the mucosal protective factors, such as the production of gastric mucus, membrane barriers to permeability, or mucosal cell turnover time.

Single or multiple gastric or duodenal ulcers are often directly related to stress, including psychological stress and stress related to trauma such as burns, surgery, shock, and the like.

The use of salicylates, especially aspirin and aspirin derivatives, to combat pain, inflammation and fever is accepted medical practice. The salicylates are used in especially large quantities for treating rheumatic and arthritic disorders; REPORT ON RHEUMATIC DISEASES No. 33, London, The Arthritis and Rheumatism Council, 1968.

It is becoming widely recognized that irritation of the gastric mucosa, often leading to frank ulceration of the walls of the gastrointestinal tract, is an especially troublesome side effect associated with the prolonged use of salicylate drugs, especially aspirin. A listing of references relating to salicylate analgesics and contraindications appears in Martindale, THE EXTRA PHARMACOPOEIA, 26th Ed., The Pharmaceutical Press, London, pp. 221-227.

By the present invention, zwitterionic surfactant-type compounds are administered orally to decrease or prevent stress-induced or salicylate-induced ulceration of the gastrointestinal tract.

BACKGROUND ART

Long-chain materials have been suggested for use in the treatment of gastric and duodenal ulcers: J5-2025-706 and J5 2025-711. These two Japanese patents relate, respectively, to polyunsaturated long-chain alcohols and polyunsaturated esters of long-chain alcohols.

A $C_{22}$ homolog of retinoic acid and its salts are stated to be effective for promoting wound healing. The acid or the salt can be applied directly to the wound as a solution, ointment or powder; U.S. Pat. No. 3,689,667 (1972); also, U.S. Pat. No. 3,966,967; 3,882,244; and 3,934,028, all relating to long-chain retinoic acid derivatives for the treatment of acne and psoriasis.

The interaction of zwitterionic alkyl betaine surfactants with biological membranes has been studied by Allen, et al., FEBS LETTERS, September 1975, 158. The authors conclude that the zwitterionics tested, at low concentrations and under mild conditions, can induce a high degree of membrane dissociation together with considerable preservation of enzymic activity.

Richter, et al., *Pharmazie* 27, #9, 589-94 (1972) report the effect of surface active agents on artificial (hydrophilic) membranes. The effect of various surfactants (not, apparently, including zwitterionics) on membrane transport in synthetic membranes was studied.

Lore and Luciano, *Physiology and Behavior* 18, 743-45 (1977) have observed that stress phenomena cause ulcers in rats in a laboratory test situation and propose physiologic mechanisms to explain this observation.

DISCLOSURE OF INVENTION

The present invention encompasses compositions and means for treating and/or preventing ulcers in humans and lower animals. Certain zwitterionic surfactant-type compounds are provided in convenient unit dosage form for oral administration to the ulcer patient.

The present invention also encompasses compositions and means for safely treating pain, inflammation and fever in animals, especially in humans. An effective amount of a salicylate drug compound is used in conjunction with an effective amount of certain zwitterionic anti-ulcer compounds. The salicylate and zwitterionic compounds act in concert to provide the usual analgesic, anti-inflammatory and antipyretic benefits associated with the use of salicylate drugs, but with reduced ulceration of the gastric (including duodenal) mucosa.

The invention also encompasses treatment regimens comprising orally administering an effective amount of the salicylate-based drug and an effective amount of the zwitterionic surfactant compound to an animal, especially a human, suffering from tissue inflammation, pain or fever.

BEST MODE

The zwitterionic compounds used in the practice of this invention and their synthesis are described in detail, hereinafter.

The salicylate compositions and treatment regimens of this invention employ: (1) a safe and effective amount of a pharmaceutically-acceptable salicylate-based drug, especially aspirin; and (2) a safe and effective amount of the zwitterionic, especially the $C_{20}$ to $C_{24}$ ammoniohexanoate zwitterionics. These compounds are administered orally to a patient in need of salicylate therapy.

By "safe and effective amount of salicylate-based drug" herein is meant sufficient salicylate compound to alleviate tissue inflammation, pain and/or fever at a reasonable benefit/risk ratio attendant with any medical treatment. Within the scope of sound medical judgment, the dosage of salicylate compound will vary with the particular condition being treated, the severity of the condition, the duration of the treatment, and the specific salicylate compound employed. The salicylate drugs are so well known and widely used that the selection of an appropriate dosage is well within the skill of the practitioner.

By "safe and effective amount of the zwitterionic surfactant compound" herein is meant a sufficient amount of the zwitterionic compound to decrease or prevent gastrointestinal irritation or ulceration caused by stress or by the salicylate drug. Within the scope of sound medical judgment, the dosage of zwitterionic surfactant compound will vary with the needs of the patient, e.g., with the intensity and duration of salicylate therapy.

By "pharmaceutically-acceptable" herein is meant that the drug-active compounds and other ingredients used in the present compositions and processes are suitable for use in contact with the tissues of humans and lower animals without undue toxicity, irrritation, allergic response, and the like, commensurate with a reasonable benefit/risk ratio.

When used to prevent salicylate-induced ulceration, the present invention is most conveniently carried out by orally administering compositions comprising both the zwitterionic surfactant compound and the compatible salicylate drug compound and, optionally, compatible carrier materials. Alternatively, the zwitterionic and salicylate compounds can be orally administered separately, in which case it is preferred to administer the zwitterionic surfactant concurrently with or within three hours after the salicylate drug.

By the term "comprising" as used herein is meant that various other, compatible drugs and medicaments, as well as inert ingredients, can be conjointly employed in the compositions and processes of this invention, as long as the zwitterionic compound and salicylate-based drug are used in the manner disclosed. The term "comprising" thus encompasses and includes the more restrictive terms "consisting of" and "consisting essentially of" which characterize the use of the zwitterionic and salicylate compounds.

By "compatible" herein is meant that the components of the compositions are capable of being commingled without interacting in a manner which would substantially decrease the efficacy of the total compositions under ordinary use situations.

By "carrier" herein is meant an ingestible fluid or solid material which can optionally be used to provide finished compositions for oral use. Dry compositions are storage-stable and preferred in the practice of this invention.

All percentages herein are by weight, unless otherwise specified.

The zwitterionic compounds and salicylate compounds critical to the practice of this invention are disclosed more fully hereinafter. Optional ingredients which can be included in the compositions to provide aesthetic and convenience benefits, but which are not critical to the practice of the invention, are also disclosed.

SALICYLATES

The salicylate-based compounds used herein comprise salicylic acid, or derivatives thereof. Salicylic acid (o-hydroxybenzoic acid) is represented by the formula

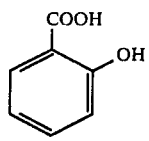

and can be derivatized at both the hydroxyl and carboxyl groups to provide various pharmacologically-active analgesic, anti-inflammatory and/or antipyretic agents. The salicylate-based drugs employed in the practice of this invention are all well known in the medical arts and their drug activity in humans and lower animals is well documented.

Salicylic acid, its pharmaceutically-acceptable salts, and its pharmaceutically-acceptable esters and derivatives are used herein. Non-limiting examples of such materials include: sodium salicylate, acetylsalicylic acid (aspirin; preferred herein), aloxiprin (a polymeric condensation product of aluminum oxide and aspirin), calcium carbaspirin (calcium acetylsalicylateurea complex), choline salicylate ([2-hydroxyethyl]trimethylammonium salicylate), salicoside, salicylamide (o-hydroxybenzamide), acetylsalicylsalicylic acid, sodium thiosalicylate, magnesium salicylate and salicylsulfuric acid. All of the foregoing materials are commercially available and are well-recognized drug agents.

Other salicylic acid derivatives useful in the present compositions and processes are substituted salicylates of the formula (I), as follows:

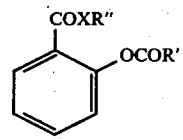

wherein R' is an alkyl substituent, especially alkyl having from 1 to 4 carbon atoms, X is O, NH or NR" and R" is a saturated or unsaturated aliphatic substituent having from 4 to 10 carbon atoms, benzyl or phenyl. The term "saturated or unsaturated aliphatic substituent" includes alkyl, alkenyl, alkadienyl, alkatrienyl, alkynyl and alkadiynyl groups.

The R" moiety can be unsubstituted or can be substituted with acetoxy; alkyloxy, e.g., methoxy, ethoxy and butoxy; alkylamido; halogen, e.g., chloro, bromo and fluoro; amino; nitro; alkyl, e.g., methyl, ethyl and butyl; amido; hydroxy and like groups, without adversely affecting the overall efficacy of the salicylic acid derivative. Such groups can be in the ortho, meta or para positions when R" is benzyl or phenyl.

In general, the compounds of formula (I) are prepared from salicylic acid using standard organic synthetic techniques. In a representative synthesis scheme, salicylic acid is initially acylated with an appropriate acid anhydride of the formula $(R'CO)_2O$ wherein R' has from 1 to 4 carbon atoms. Examples of the anhydride are acetic anhydride, propionic anhydride, butyric anhydride, valeric anhydride and pivalyl anhydride. The reaction proceeds in the presence of sulfuric acid at a temperature from 40° C. to 80° C.

The resulting acyloxy benzoic acid is next reacted to form an ester (X=O) or an amide (X=R"). Esterification is carried out by first reacting the acyloxy benzoic acid with oxalyl chloride or sulfuryl chloride to provide the corresponding acyloxy benzoyl chloride. This compound is then reacted with the appropriate alcohol in the presence of pyridine in standard fashion to provide the desired formula (I) ester. Examples of suitable alcohols include primary, secondary and tertiary -butanol, -pentanol, -hexanol, -heptanol and -octanol; unsaturated alcohols, e.g., 2-butenol, 2-hexenol, 4-hexenol, 2-octenol and 3-octenol; benzyl alcohol; and phenol.

The amide compounds of formula (I) are prepared by reacting the aforesaid acyloxy benzoyl chloride with the appropriate amine at a temperature of 0° C. to 30° C., in standard fashion. When a secondary amine of the formula $NH(R'')_2$ is used, the two R'' groups may be the same or different.

Preferred salicylic acid derivatives of formula (I) are those wherein X is oxygen.

The following compounds represent further examples of salicylic acid-type drug agents of formula (I) suitable for use herein.

Butyl 2-acetoxybenzoate
Hexyl 2-acetoxybenzoate
2'-ethylhexyl 2-acetoxybenzoate
Octyl 2-acetoxybenzoate
Pentyl 2-propionoxybenzoate
Octyl 2-propionoxybenzoate
Hexyl 2-pivaloxybenzoate
Hexyl 2-butyroxybenzoate
2'-5'-Hexadienyl 2-acetoxybenzoate
2'-Hexenyl 2-acetoxybenzoate
Benzyl 2-butyroxybenzoate
Benzyl 2-acetoxybenzoate
Benzyl 2-pivaloxybenzoate
Phenyl 2-acetoxybenzoate
2-Acetoxy-N-hexylbenzamide
2-Propionoxy-N-octylbenzamide
2-Acetoxy-N,N-dibutylbenzamide
p-Acetamidophenyl 2-acetoxybenzoate
5'-Hydroxyhexyl 2-acetoxybenzoate
6'-Acetoxyhexyl 2-acetoxybenzoate
6'-Fluorohexyl 2-acetoxybenzoate
6'-Nitrohexyl 2-acetoxybenzoate
6'-Methylamidohexyl 2-acetoxybenzoate
2'-Ethyl-2'-5'-hexadienyl 2-acetoxybenzoate
2'-Acetoxybenzyl 2-propionoxybenzoate
2'-Fluorobenzyl 2-acetoxybenzoate
2'-Hydroxybenzyl 2-acetoxybenzoate
2'-Methoxybenzyl 2-acetoxybenzoate
2',4'-Diacetoxybenzyl 2-acetoxybenzoate
2'-Acetamidobenzyl 2-acetoxybenzoate

ZWITTERIONIC ANTI-ULCER COMPOUNDS

The zwitterionic compounds used in the practice of this invention are of the general formula

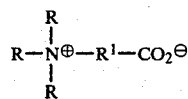

(A)

wherein: M is nitrogen (preferred) or phosphorus; at least one R group is a $C_{10}$ or longer lipophilic substituent; and $R^1$ is a hydrocarbylene substituent having a chain length preferably no greater than about 11 carbon atoms.

Ester salts of the formula (A) zwitterionics can also be used herein. Such compounds are of the formula

wherein $R^2$ is a hydrocarbyl substituent, e.g., methyl, ethyl, propyl, etc., and X is a halogen ion, especially bromide. Such esters are included in the term "zwitterionic anti-ulcer compound" as used herein.

The zwitterionic compounds and esters can be prepared by standard synthetic organic techniques; see U.S. Pat. No. 3,504,024 (1970) and British Pat. No. 1,355,055 (1974), the disclosures of which are incorporated herein by reference.

The synthesis of the preferred ammonio hexanoate zwitterionic anti-ulcer compounds (M is nitrogen; $R^1$ is $-CH_2(CH_2)_3CH_2-$) is described in detail, hereinafter.

It has been determined that only those zwitterionic compounds wherein at least one lipophilic R group contains ten or more carbon atoms exhibit the desirable pharmacologic activity disclosed herein. In general, the preferred zwitterionic surfactant compounds herein are of the formula

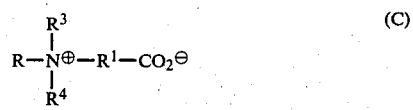

or hydrolyzable esters thereof, per formula (B).

The preferred formula (C) compounds are characterized by: R as a $C_{10}$ or higher hydrocarbyl moiety, especially tetradecyl through about tetracosyl; $R^3$ and $R^4$, which may be the same (preferred) or different hydrocarbyl moieties in the manner of R, but smaller than $C_{10}$, preferably both methyl; and $R^1$ is a $C_1-C_{10}$ hydrocarbyl moiety, preferably $C_1-C_7$ hydrocarbyl, with pentamethylene being the most preferred.

The most highly preferred zwitterionics used in the practice of this invention with salicylate drugs are those of formula (C) (or the formula (B) ester form), wherein R is eicosyl (most preferred) to about tetracosyl; $R^3$ and $R^4$ are each short-chain alkyl, e.g., methyl, ethyl and propyl, and $R^1$ is pentamethylene.

The most highly preferred zwitterionics for general therapeutic and/or prophylactic use in compositions not containing salicylate drugs are those of formula (C) (or the formula (B) ester form) wherein R is decyl ($C_{10}$) through about octadecyl ($C_{18}$), with tetradecyl ($C_{14}$) being most preferred.

The zwitterionic compounds herein can also have two of the shorter chain R groups (e.g., $R^3$ and $R^4$ in formula (C)) joined with substituent M at the cationic portion of the molecule to provide a heteroatom ring, e.g., morpholinio, and the like. Such compounds are also useful in the practice of the present invention.

It is to be understood that zwitterionic compounds defined by the foregoing formulae all exhibit the desirable pharmacological activity disclosed herein. Some of the compounds are more pharmacologically active than others and these are preferred for drug use. Some of the compounds are less stable than others, and are less preferred for that reason. In particular, the compounds wherein $R^1$ is ethylene are considerably less stable than the others so additional care in manufacture and storage is required.

The ammonio hexanoate compounds are readily prepared and have good stability. The preparation of these preferred zwitterionics is as follows. The other zwitterionics can be prepared in the manner disclosed in standard references and patents, as noted above.

PREPARATION OF AMMONIO HEXANOATE ZWITTERIONICS

The following reaction sequence can be conveniently used to prepare the preferred ammonio hexanoate compounds ($R^1$ is pentamethylene) used in the practice of this invention. All starting materials are commercially available.

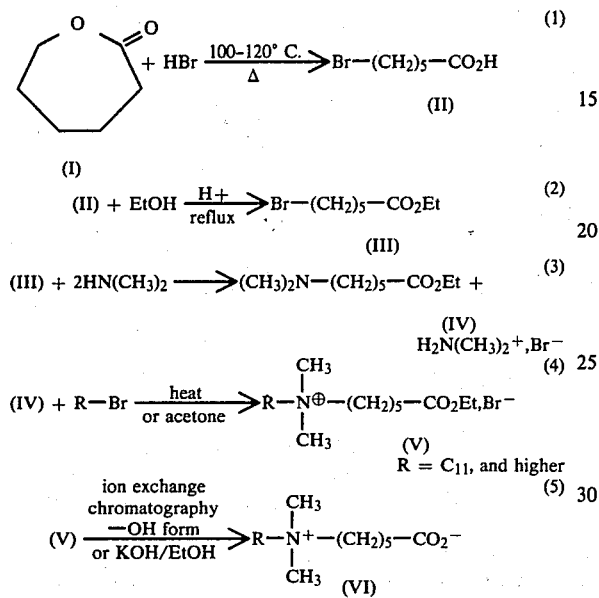

The cleavage of lactone (I) is readily achieved by either HBr or HCl in the presence or absence of a catalyst. If done in a closed system under pressure at 120° C., the reaction is complete in two hours and yields ranging from 50–95% can be obtained. Bromoacid (II) is essentially quantitatively converted to ester (III) by refluxing for 3 hours in ethanol containing a catalytic amount of anhydrous HCl or HBr.

Amination of the bromoester (reaction 3) takes place at ambient temperatures and atmospheric pressure with no solvent. The reaction is exothermic and the heat generated aids in driving the reaction to completion. The effect of increased temperature and pressure on the yield of aminoester (IV) is minimal. After workup and distillation, yields as high as 97% are obtained.

The quaternization of the aminoester (reaction 4) is achieved in yields ranging from 75–95% depending on solvent, temperature and reaction time. Ideally, a 1:1 mixture of the aminoester and appropriate alkylbromide is heated neat or refluxed in alcohol or acetonitrile solution at 95°–120° C. for 2–3 hours. The crude quaternary ester (V) can be crystallized from ether or dissolved in ethanol and used directly in the hydrolysis step. The quaternary esters can also be made by the reaction of alkyldimethylamine and bromoester (III). However, with the longer chain amines ($C_{18}$ and higher) appreciable amounts of elimination produce (olefin) are obtained.

The hydrolysis of the quaternary ester (reaction 5) can be performed under a variety of conditions giving rise to a wide range of yields and workup procedures. By far the most efficient method is that of ion-exchange chromatography. Thus, an aqueous or alcoholic solution of (V) is treated on an $^-$OH form anion exchange resin. The exchange of bromide for hydroxide and subsequent hydrolysis occur within a few hours. The desired zwitterionic material (VI) is obtained essentially free of inorganic bromides. This method represents a considerable improvement over alcoholic hydrolysis under reflux in that formation (and removal) of inorganic halides is not involved in the reaction and product isolation. Representative examples of the ammonio hexanoate zwitterionic compounds which can be prepared in the foregoing manner and used in the practice of this invention include the following (where AH represents the N,N-dimetylammoniohexanoate moiety): n-undecyl AH; n-dodecyl AH; n-tridecyl AH; n-tetradecyl AH; n-pentadecyl AH; n-hexadecyl AH; n-heptadecyl AH; n-octadecyl AH; n-nonadecyl AH; n-eicosyl AH; n-heneicosyl AH; n-docosyl AH; n-tricosyl AH; n-tetracosyl AH; n-pentacosyl AH; n-hexacosyl AH; n-heptacosyl AH; n-octacosyl AH; n-nonacosyl AH; and n-triacontyl AH.

The corresponding $C_{10}$ and higher ammonio and phosphonio acetates, propionates, butyrates and pentanoates can be prepared using corresponding organic chemical techniques and used in the practice of this invention. The synthesis of representative zwitterionic compounds is as follows.

Preparation of n-$C_{14}H_{29}N^{\oplus}(CH_3)_2(CH_2)_5CO_2^{\ominus}$

A neat solution of tetradecylbromide (55.4 g) and ethyl 6-dimethylammoniohexanoate prepared in the manner disclosed in CA 59 10560 (34.32 g) was heated (90° C.) overnight (18 hours), cooled to room temperature and triturated with petroleum ether (3×0.25 l). Ethyl 6-dimethyltetradecylammoniohexanoate bromide (67.0 g) was isolated upon filtration of a cold ethanol solution.

The quaternary ester bromide (67.0 g) was diluted in 90/10 ethanol/water (0.20 l) and eluted through successive ion-exchange columns containing base resin (Rexyn 201; 433.0 g wet) and mixed-bed resin (Rexyn 300; 200.0 g wet). The product solution was evaporated to dryness and the residue crystallized from acetone/hexane as white crystals of the title compound.

The n-$C_{14}H_{29}N^{\oplus}(CH_3)_2(CH_2)_5CO_2^{\ominus}$ compound is the most preferred zwitterionic for prophylaxis and therapy of duodenal and gastric ulcers in compositions not containing salicylate drugs.

In like fashion are prepared the following n-tetradecyl ammonio hexanoate compounds: N,N-diethyl; N,N-dipropyl; and N-methyl N-ethyl.

Preparation of n-$C_{20}H_{41}N^{\oplus}(CH_3)_2(CH_2)_5CO_2^{\ominus}$

Eicosyl chloride (86.8 g), ethyl 6-dimethylaminohexanoate (51.5 g) and sodium iodide (0.30 g; Baker) hexanoate (51.5 g) and sodium iodide (0.30 g; Baker) were refluxed in acetonitrile (150 ml) overnight (16 hours). The reaction mixture was evaporated to dryness, and the residue washed in ether (3×0.20 l) and dried to produce the ethyl 6-eicosyldimethylammoniohexanoate bromide (130.0 g).

The quaternary ester bromide (64.0 g) was dissolved in 95% EtOH (1.20 l) and eluted through successive ion-exchange columns containing base resin (Rexyn 201; 170 g wet) and mixed-bed resin (Rexyn 300; 60 g wet). The final ethanolic solution was evaporated to dryness and the residue dried and crystallized from acetonehexane to produce white crystals of the title compound.

The n-$C_{20}H_{41}N^{\oplus}(CH_3)_2(CH_2)_5CO_2^{\ominus}$ compound is the most preferred zwitterionic for use in combination with salicylate drugs such as aspirin to reduce salicylate-induced gastric damage.

Preparation of n-$C_{22}H_{45}N^{\oplus}(CH_3)_2(CH_2)_5CO_2^{\ominus}$

Docosylbromide (10.0 g) and ethyl 6-dimethylaminohexanoate (4.60 g) were diluted in ethanol (10.0 ml) and refluxed overnight (18 hours). The reaction mixture was evaporated to dryness, washed with ether (2×50 ml) and crystallized from acetone to produce white crystals of ethyl 6-dimethyldocosylammoniohexanoate bromide.

The quaternary ester bromide (9.0 g) was diluted in 90/10 ethanol/water (20 ml) and eluted successively through ion-exchange columns containing base resin (Rexyn 201 (HO); 10.0 g wet) and mixed-bed resin (Rexyn 300 (H-OH); 5.0 g wet). The final solution was evaporated to dryness and crystallized from $CHCl_3$/acetone to yield white crystals of the title compound.

Preparation of n-$C_{22}H_{45}N^{\oplus}(CH_3)_2(CH_2)_{10}CO_2^{\ominus}$

A solution of methyl 11-dimethylaminoundecanoate ester (3.30 g), prepared in the manner disclosed in CA 56 10027, and commerical docosylbromide (5.50 g) in acetonitrile (20 ml) was heated at reflux overnight. The reaction mixture was evaporated to dryness under reduced pressure, 50 ml of 90/10 ethanol/water added, and the solution eluted successively through a column of base resin (50.0 g; Rexyl 300 (H-OH)). The eluant was evaporated to dryness to produce the zwitterion as an off-white solid, which crystallized from a solution of methanol-acetone as white crystals of the title compound.

INDUSTRIAL APPLICABILITY

Those aspects of the present invention which relate to salicylate therapy are most conveniently practiced by orally administering compositions which comprise mixtures of the salicylate-based drug and the zwitterionic. In an alternate mode, a dosage regimen can consist of separate administration of the two types of agents, but this is less convenient.

For optimal anti-ulceration results the zwitterionic is administered orally concurrently with or within about three hours after administration of the salicylate drug. However, habitual users of salicylate drugs commonly use such drugs more frequently than three-hour intervals. Since the zwitterionic remains in the stomach at least three hours, the protective benefit is achieved even when the zwitterionic and salicylate are administered concurrently as part of a regular salicylate-based therapeutic regimen.

Especially useful compositions herein for oral administration comprise, in unit dosage form, from about 10 mg to about 500 mg of acetylsalicyclic acid (aspirin) and from about 180 mg to about 2000 mg of the zwitterionic compound.

Those aspects of this invention which relate to ulcer therapy and/or prophylaxis without concurrent salicylate therapy comprise simply administering the zwitterionic orally. Any convenient oral dosage form can be used, and single dosages can range from about 18 mg to 2500 mg. Multiple dosages can be administered daily, as needed. Optimally, the zwitterionic is administered prior to mealtimes, but it has been found that food protein does not interfere with anti-ulcer activity.

Of course, the total daily usage of the compositions herein will be decided by the attending physician. For example, the usage rate for combined salicylate/zwitterionic compositions will be determined by such factors as the type of disease state being treated, the age and weight of the patient, the severity of the condition, the length of time the patient will be undergoing salicylate therapy and like factors well known in the medical arts. In general, oral treatment regimens according to the present invention comprise orally administering to a human or lower animal in need of such treatment from about 50 mg to about 6000 mg (preferably 100–1000 mg) of salicylate drug, especially aspirin, per day and from about 20 mg/kg to about 3000 mg/kg (preferably 25 mg/kg –100 mg/kg) per day of the zwitterionic surfactant, especially $C_{20}AH$, per day. (By "mg/kg" herein is meant milligrams per kilogram of patient body weight; see *Animal Testing*, hereinafter).

Likewise, for ulcer therapy and/or prophylaxis, the usage rate and term of treatment will depend on the severity of ulceration, diet and overall physical and psychological state of the patient.

For purposes of oral administration, the compositions of this invention can be formulated as capsules, tablets or granules. For treatment of non-human animals, the compositions are preferably incorporated in animal feeds, feed supplements or feed concentrates.

The compositions of the present type are orally administered, preferably in unit dosage form in combination with excipients such as solid or liquid fillers, diluents or encapsulating substances which provide a pharmaceutical carrier, e.g., materials commonly used in the manufacture of tablets, capsules, elixirs, and the like. Some examples of the substances which can serve as pharmaceutical carriers herein include sugars such as lactose, glucose and sucrose; starches such as corn starch and potato starch; cellulose and its derivatives, such as sodium carboxymethylcellulose, ethylcellulose and cellulose acetate; powdered gums; malt; gelatin; stearic acid; calcium sulfate; vegetable oils, such as peanut oil and cottonseed oil; mineral oil; polyols such as propylene glycol, glycerin, sorbitol, mannitol and polyethylene glycol; agar; alginic acid; as well as other non-toxic, compatible substances used in pharmaceutical formulations. Wetting agents and lubricants, coloring agents, flavoring agents and preservatives can also be present. Enteric coatings can be used in standard fashion to provide prolonged release of the compositions and/or release in the intestines rather than in the stomach.

The compositions herein can also optionally contain an effective amount of an antacid. Aluminum hydroxide (hydrated alumina, available as Amphojel®, Aldrox®, etc.), magnesium oxide, magnesium carbonate, calcium carbonate, magnesium trisilicate, magnesium hydroxide, and mixed magnesium/aluminum oxides and hydroxides, all of which are well-known antacids used in the management of duodenal and gastric ulcers, can be incorporated in the compositions of the present invention.

The compositions herein can be prepared by formulation and tableting techniques commonly used in the pharmaceutical industry.

The following demonstrates in vivo utility of the compositions herein in the management of ulceration of the gastric mucosa induced by various means. It is generally accepted that a simple type of animal test is probably insufficient to establish, with certainty, which member of a class of effective anti-ulcer agents will prove most effective for human use. Following standard practice, a battery of animal studies were employed to help determine the overall best zwitterionic anti-ulcer agent of the type disclosed herein. The animal tests also established that optimal anti-ulcer activity for the zwitterionics is at least about 18–25 mg/kg. While higher dosages can be used, dosages of 25 mg/kg/day are conveniently administered, orally.

ANIMAL TESTING

I. Mechanical Stress-Induced Gastric Ulcers

One hundred male, albino Sprague-Dawley rats (CD strain) were used in each stress-induced ulcer study. All of the rats were acclimated for one week. Mechanical restraint was initiated after a 24-hour fasting period and the rats weighed 135–160 g at that time.

The test materials used in the study were the following N,N-dimethyl zwitterionics: n-$C_{14}H_{29}$ ammoniohexanoate ($C_{14}AH$), n-$C_{18}H_{37}$ ammoniohexanoate, n-$C_{20}H_{41}$ ammoniohexanoate ($C_{20}AH$) and n-$C_{22}H_{45}$ ammoniohexanoate, as well as Maalox® and cimetidine (as Tagamet®).

With the exception of the two commerical preparations used in the study, the zwitterionic compounds listed were prepared as 2% solutions in 100 milliliters of triple distilled water. A 2% cimetidine suspension was prepared in 0.5% methyl cellulose. Maalox® was already in liquid form. All test solutions were continuously stirred during dosing. The amount of compound administered was based on the body weight of each rat; the dosage rate was 100 mg/kg.

Following a 24-hour fasting period, 80 of the 100 rats were restrained with 12"×12" fine copper wire screen. The other 20 were used in the compound control group. The animals were divided into five test groups of 20 rats each and dosed according to the following schedule:

| Group | Treatment |
| --- | --- |
| I | stress + water |
| II | stress + 100 mg/kg body weight of compound after 0 hour stress |
| III | stress + 100 mg/kg body weight of compound after 6 hours stress |
| IV | stress + 100 mg/kg body weight of compound after 12 hours stress |
| V | 100 mg/kg body weight of compound after 0 hours, no stress |

Mechanical restraint was continued after compound dosing and all rats were sacrificed by $CO_2$ at 48 hours after initiating the fast.

The stomachs were removed, cut along the greater curvature and rinsed with 0.9% normal saline. The stomachs were blind graded for gastric lesions using a stereoscopic microscope (10× magnification).

In tests of the foregoing type, the zwitterionic compounds provided a substantial reduction in stomach ulceration.

II. Aspirin-Induced Gastric Lesions and Bleeding

Thirty male, albino Sprague-Dawley rats (CD strain) were used in each aspirin-induced ulcer study. After acclimating for one week, each rat was fasted for 30 hours with free access to water during the first 24 hours. These rats weighed 135–160 g at the time of initial dosing.

Reagents and Methods a. 0.5% methyl cellulose (MC) was prepared by suspending an appropriate amount of powder in triple distilled water. The suspension was heated to 60° C. and stirred for 10–20 minutes. Refrigeration of the heated sample for 4–6 hours yielded a fine, homogeneous suspension which was refrigerated until use.

b. The stock bottle of aspirin (ASA) was kept desiccated at room temperature until use. Twenty-four hours before scheduled dosing, two 0.800 g samples of ASA were weighed and put into small glass vials. These vials were also desiccated until time of testing.

Immediately before dosing, the weighed sample of ASA was poured into a mortar. By adding one milliliter at a time, the ASA was ground into the 0.5% MC suspension to a volume of 20 milliliters. This 4% ASA suspension was dosed at a level of 200 mg/kg body weight of the rat. This dose rate was equivalent to a volume dose of 1 ml/200 g body weight.

c. The zwitterionic compounds were usually dissolved in triple distilled water. Those that were not water-soluble were suspended in 0.5% MC the same way as ASA. The 2% test compound solutions were dosed at 100 mg/kg body weight. As before, the following N,N-dimethyl zwitterionics were among those tested: $C_{14}$ ammoniohexanoate; $C_{16}$ ammoniohexanoate; $C_{18}$ ammoniohexanoate; $C_{20}$ ammoniohexanoate ($C_{20}AH$); and $C_{22}$ ammoniohexanoate. A $C_{14}$ quaternary ammonium bromide and commercial cimetidine (as Tagamet®) were also included in the study.

d. All triple distilled water and 0.5% MC doses were given as 1 ml/200 g body weight of the rat.

Three groups, each comprising ten rats, were tested with each compound. The treatment groups were as follows: 0.5% MC+water; ASA+water; ASA+test compound.

After 24 hours fasting, ASA was administered by gavage at a level of 200 mg/kg body weight of the rat. Either immediately prior to or 3 hours after ASA, the test compound was also given by gavage at a level of 100 mg/kg body weight. Fasting was continued without water. All rats were sacrificed by $CO_2$ at 6 hours after being given ASA. The stomachs were removed and cut along the greater curvature.

After rinsing out the stomach contents with 0.9% normal saline, the stomachs were blind graded for gastric lesions using a stereoscopic microscope (10X). The severity and incidence of gastric lesions and bleeding were graded.

In tests of the foregoing type, the $C_{20}AH$ and $C_{22}AH$ provided a substantial reduction in stomach ulceration.

III. Cysteamine-Induced Duodenal Ulcer

Male Charles River Sprague-Dawley rats of a body weight of 190 to 220 g were used in this test. Cysteamine HCl (2-mercaptoethylammonium chloride, $HSCH_2CH_2NH_3^{\oplus}$, $Cl^{\ominus}$) was injected once subcutaneously in the morning at 390 or 425 mg/kg in 0.5 ml of water. The rats were fasted 24 hours before and after cysteamine HCl injection and were sacrificed 24 hours after injection. Drug or vehicle treatments were initiated immediately after cysteamine HCl injection and given at various periods after the cysteamine HCl. After the rats were sacrificed, the stomach and duodenum were dissected, opened along the greater curvature of the stomach and the mesenteric attachment for the duodenum and were examined with a stereoscopic microscope at 7× magnification for the presence of lesions. The area, number and severity of the ulcers were determined and an ulcer grade based on severity (erosions=1, surface lesion=2, deep lesion=3 and perforated lesion=4) and number of ulcers was calculated.

In tests of the foregoing type, the $C_{12}AH$, $C_{14}AH$, $C_{16}AH$ and $C_{20}AH$ zwitterionics inhibited either severity or incidence of duodenal ulcers, or both.

IV. Pylorus-Ligation Gastric Ulcer ("Shay Rat")

Charles River Sprague-Dawley rats weighing 220-300 g were fasted 24 hours prior to ligation. The animals were shaved under the right rib cage, anesthetized with absolute ether $(C_2H_5)_2O$ and opened transversely under the right rib cage. The pylorus was ligated with #0000 surgical silk and the skin of the animal was sutured with #0000 surgical silk. The hide was brought in apposition and held with 9 mm stainless steel autoclips. The animals were dosed while anesthetized. When the route of dosing was oral, #8 Rusch rubber catheter was intubated at a maximum of 4 inches. When the route was intraperitoneal (IP) injection, a sterile disposable Plastipak syringe was used with a 25 gauge, ⅝" sterile disposable Yale needle. Eighteen hours after ligation the animals were sacrificed using $CO_2$. The animals were opened ventrally and the stomachs excised. The stomachs were opened along the greater curvature, rinsed in 0.9% saline and placed upon a white index card to be viewed for ulceration under a stereoscopic microscope. Before grading, the mucosa was swabbed with cotton-tipped applicators. This helped evaluate the mucus properties and spread the tissue for a more thorough examination.

In tests of the foregoing type, the $C_{12}AH$, $C_{14}AH$, $C_{16}AH$, $C_{18}AH$, $C_{20}AH$ and $C_{22}AH$ compounds (dosed at 100 mg/kg) all produced lower incidences of ulcers in the test animals as compared with controls. With the exception of the salicylate model, best overall performance from the battery of tests run was noted for the $C_{14}$, $C_{16}$ and $C_{18}$ compounds.

The reduction in ulcer incidence in the Shay Rat test generally paralleled the suppression of pepsin activity by the zwitterionics, as measured in vitro. The $C_{14}AH$, $C_{16}AH$, $C_{18}AH$, $C_{20}AH$ and $C_{22}AH$ compounds are all quite effective for suppressing pepsin activity.

As can be seen from the foregoing, the zwitterionic compounds disclosed herein, especially the decyl through about tetracosyl N,N-dimethylammoniohexanoate ($C_{10}AH$ through $C_{24}AH$) compounds, provide effective prophylaxis and therapy for both gastric and duodenal ulcers.

The following examples illustrate the present compositions and their use, but are not intended to be limiting of the scope of the invention. In the examples the compounds $C_{12}AH$, $C_{14}AH$, $C_{16}AH$, $C_{18}AH$, $C_{20}AH$, $C_{22}AH$ and $C_{24}AH$ are the n-$C_{12}H_{25}N^{\oplus}(CH_3)_2(CH_2)_5CO_2^{\ominus}$, n-$C_{14}H_{29}N^{\oplus}(CH_3)_2(CH_2)_5CO_2^{\ominus}$, n-$C_{16}H_{33}N^{\oplus}(CH_3)_2(CH_2)_5CO_2^{\ominus}$, n-$C_{18}H_{37}N^{\oplus}(CH_3)_2(CH_2)_5CO_2^{\ominus}$, n-$C_{20}H_{41}N^{\oplus}(CH_3)_2(CH_2)_5CO_2^{\ominus}$, n-$C_{22}H_{45}N^{\oplus}(CH_3)_2(CH_2)_5CO_2^{\ominus}$ and n-$C_{24}H_{49}N^{\oplus}(CH_3)_2(CH_2)_5CO_2^{\ominus}$ compounds, prepared in the manner as disclosed above.

EXAMPLE I

Capsules are prepared by conventional methods, as follows:

| Ingredient | mg. per capsule |
|---|---|
| $C_{20}AH$ | 150 |
| Acetylsalicylic acid | 500 |

Two capules of the above type are administered orally at three hour intervals four times daily to substantially reduce the pain and inflammation associated with arthritis, rheumatism, bursitis and lumbago, without stomach ulceration.

In the capsules of Example I, the acetylsalicylic acid (aspirin) is replaced by an equivalent amount of sodium salicylate, aloxiprin, calcium carbaspirin, choline salicylate, salicoside, salicylamide, acetylsalicylsalicylic acid, sodium thiosalicylate, magnesium salicylate and salicylsulfuric acid, respectively, and equivalent results are secured.

In the capsules of Example I the $C_{20}AH$ is replaced by 200 mg. of $C_{22}AH$ and $C_{24}AH$, respectively, and equivalent results are secured.

EXAMPLE II

Tablets are prepared by conventional methods, as follows:

| Ingredient | mg. per tablet |
|---|---|
| $C_{20}AH$ | 100 |
| Acetylsalicylic acid | 250 |
| Starch | 50 |
| Lactose | 50 |
| Hydrated alumina* | 100 |
| Magnesium stearate** | 1.5 |

*Conventional antacid
**Tableting aid and lubricant

Two capsules of the above type are administered orally six times daily to substantially reduce the pain and inflammation associated with chronic lower back pain and tendinitis, without stomach ulceration.

In the tablets of Example II, the hydrated alumina is replaced by an equivalent amount of magnesium oxide, magnesium carbonate, mixed magnesium/aluminum oxides and hydroxides, calcium carbonate, magnesium trisilicate, and magnesium hydroxide, respectively, and equivalent results are secured.

EXAMPLE III

Standard pharmaceutical gelatin capsules containing 500 mg. of $C_{12}AH$, $C_{14}AH$, $C_{16}AH$, $C_{18}AH$, $C_{20}AH$ and $C_{22}AH$ compounds, respectively, are prepared using conventional methods.

One 500 mg. gelatin capsule of any of the foregoing is administered orally four times daily at regular intervals (preferably before mealtimes and at bedtime) to reduce the incidence of ulceration of the gastrointestinal mucosal lining.

EXAMPLE IV

In a modification of the capsules of Example III, the zwitterionic compounds are replaced by 500 mg. of ethyl 6-dimethyltetradecylammoniohexanoate bromide; ethyl 6-diethyltetradecylammoniohexanoate bromide; and ethyl 6-dipropyltetradecylammoniohexanoate bromide, respectively, and equivalent results are secured.

EXAMPLE V

Capsules are prepared in the manner of Example III comprising 250 mg. of magnesium-aluminum hydroxide (hydrated magnesium aluminum oxide) and 250 mg. of any of the following: $C_{12}AH$, $C_{14}AH$, $C_{16}AH$, $C_{18}AH$, $C_{20}AH$, $C_{22}AH$ and $C_{24}AH$, respectively. One capsule is administered three times daily to reduce excess stomach acidity and to reduce stomach ulceration.

EXAMPLE VI

Gelatin capsules comprising 500 mg. unit doses of the following zwitterionic compounds are prepared: n-$C_{14}H_{29}N^{\oplus}(CH_3)_2(CH_2)_3CO_2^{\ominus}$; n-$C_{16}H_{29}N^{\oplus}(C_2H_5)_2(CH_2)_6CO_2^{\ominus}$; n-$C_{18}H_{37}P^{\oplus}(CH_3)_2(CH_2)_5CO_2^{\ominus}$; and n-$C_{20}H_{41}N^{\oplus}(C_3H_7)_2(CH_2)_{10}$-$CO_2^{\ominus}$, respectively. Administered orally to a 70 kg human or animal patient four times daily for two months, the capsules provide relief from stomach and duodenal ulceration.

While the invention has thus far been described in terms of various zwitterionic compounds having their lipophilic substituent group R as alkyl, it is to be understood that other types of lipophilic R groups can replace alkyl without departing from the scope or spirit of this invention. In particular, lipophilic group R can be alkaryl. Thus, compounds such as n-$C_{12}H_{25}C_6H_4CH_2N^{\oplus}$-$(CH_3)_2(CH_2)_5CO_2^{\ominus}$ are useful anti-ulcer agents herein. (In limited animal testing, this $C_{12}$ compound was equal to $C_{14}AH$ in anti-ulcer efficacy. Such compounds can be prepared in the same manner as the alkyl zwitterionics.

EXAMPLE VII

A treatment regimen for gastric ulcers comprises orally administering to a human or animal in need of such treatment about 100 mg/kg/day of the highly preferred alkaryl zwitterionic anti-ulcer agent

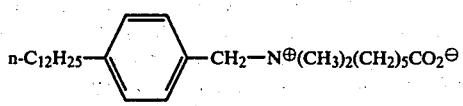

for a period of about 30 days.

In the treatment regimen of Example VII, the $C_{12}$ phenyl compound is replaced by an equivalent amount of the $C_{10}$ through $C_{20}$ phenyl compounds, respectively, and equivalent results are secured.

As can be seen from the foregoing, the present invention provides a process for treating (including preventing) ulcers in humans and lower animals in need of such treatment by oral administration of the zwitterionic compounds described herein. The invention also encompasses a process for preventing ulcers in a human or lower animal undergoing oral salicylate drug therapy by orally administering thereto a zwitterionic compound of the disclosed type concurrently with oral administration of the salicylate drug. Safe and effective amounts of conventional antacids (generally, 5 mg. to 500 mg. in unit dosage compositions) can be used in conjunction with the zwitterionics in the manner of this invention.

What is claimed is:

1. A composition of matter for oral administration comprising:
   (a) a safe and effective amount of a conventional antacid; and
   (b) a zwitterionic compound selected from the group consisting of
   n-$C_{12}H_{25}N^+(CH_3)_2(CH_2)_5CO_2^-$,
   n-$C_{14}H_{29}N^+(CH_3)_2$-$(CH_2)_5CO_2^-$,
   n-$C_{16}H_{33}N^+(CH_3)_2(CH_2)_5CO_2^-$,
   n-$C_{18}H_{37}N^+(CH_3)_2(CH_2)_5CO_2^-$,
   n-$C_{20}H_{41}N^+(CH_3)_2(CH_2)_5CO_2^-$, and
   n-$C_{22}H_{45}N^+(CH_3)_2(CH_2)_5CO_2^-$, and esters and salts thereof in an amounts which is safe and effective for preventing or relieving ulceration of the gastric mucosa.

2. A composition according to claim 1 containing from about 18 mg. to about 2,500 mg. of the zwitterionic compound.

3. A composition according to claim 2 wherein the antacid is selected from the group consisting of sodium bicarbonate, aluminum hydroxide, magnesium oxide, magnesium carbonate, magnesium-aluminum hydroxide, calcium carbonate, magnesium trisilicate, magnesium hydroxide, and mixtures thereof.

4. A composition of matter for oral administration comprising:
   (a) a safe and effective amount of a salycilate-based drug; and
   (b) a zwitterionic compound selected from the group consisting of n-$C_{12}H_{25}N^{\oplus}(CH_3)_2(CH_2)_5CO_2^{\ominus}$, n-$C_{14}H_{29}N^{\oplus}$-$(CH_3)_2(CH_2)_5CO_2^{\ominus}$, n-$C_{16}H_{33}N^{\oplus}(CH_3)_2(CH_2)_5CO_2^{\oplus}$, n-$C_{18}H_{37}N^{\oplus}$-$(CH_3)_2(CH_2)_5CO_2^{\ominus}$, n-$C_{20}H_{41}N^{\oplus}(CH_3)_2(CH_2)_5CO_2^{\ominus}$, and n-$C_{22}H_{45}N^{\oplus}(CH_3)_2(CH_2)_5CO_2^{\ominus}$, and ester salts thereof in an amount which is safe and effective for preventing or relieving ulceration of the gastric mucosa.

5. A composition according to claim 4 which comprises, in unit dosage form, from about 10 mg. to about 500 mg. of the salicylate drug and from about 180 mg. to about 2,000 mg. of the zwitterionic compound.

6. A composition according to claim 5 wherein the salicylate compound is a member selected from the group consisting of sodium salicylate, acetylsalicyclic acid, aloxiprin, calcium carbaspirin, choline salicylate, salicoside, salicylamide, acetylsalicylsalicylic acid, sodium thiosalicylate, magnesium salicylate, and salicylsulfuric acid.

7. A composition according to claim 6 wherein the zwitterionic compound is selected from the group consisting of n-$C_{20}H_{41}N^{\oplus}(CH_3)_2(CH_2)_5CO_2^{\oplus}$, n-$C_{22}H_{45}N^{\oplus}$-$(CH_3)_2(CH_2)_5CO_2^{\ominus}$, and ester salts thereof.

8. A composition according to claim 6 wherein the salicylate drug is acetylsalicyclic acid.

9. A composition according to claim 8 wherein the zwitterionic compound is n-$C_{20}H_{41}N^{\oplus}(CH_3)_2(CH_2)_5CO_2^{\ominus}$, or ester salts thereof.

10. A composition according to claim 9 in capsule or tablet form.

11. A composition according to claim 4 which contains, as an additional ingredient, a safe and effective amount of a conventional antacid.

12. A composition according to claim 11, which contains from about 5 mg. to about 500 mg. of a conventional antacid selected from the group consisting of sodium bicarbonate, aluminum hydroxide, magnesium oxide, magnesium carbonate, magnesium-aluminum hydroxide, calcium carbonate, magnesium trisilicate, magnesium hydroxide, and mixtures thereof.

13. A process for preventing or relieving ulceration of the gastric mucosa in a human or lower animal in need of such treatment by orally administering thereto at least about 18 mg/kg of body weight per day of a zwitterionic compound selected from the group consisting of n-$C_{12}H_{25}N^{\oplus}(CH_3)_2(CH_2)_5CO_2^{\ominus}$, n-$C_{14}H_{29}N^{\oplus}$-$(CH_3)_2(CH_2)_5CO_2^{\ominus}$, n-$C_{16}H_{33}N^{\oplus}(CH_3)_2(CH_2)_5CO_2^{\ominus}$, n-$C_{18}H_{37}N^{\oplus}$-$(CH_3)_2(CH_2)_5CO_2^{\ominus}$, n-$C_{20}H_{41}N^{\oplus}(CH_3)_2(CH_2)_5CO_2^{\ominus}$, and n-$C_{22}H_{45}N^{\oplus}(CH_3)_2(CH_2)_5CO_2^{\ominus}$, and ester salts thereof.

14. A process according to claim 13 wherein the dosage rate is at least about 25 mg/kg/day.

15. A process according to claim 13 wherein the zwitterionic compound is n-$C_{14}H_{29}N^{\oplus}(CH_3)_2(CH_2)_5CO_2^{\ominus}$, or an ester salt thereof.

16. A process according to claim 13 wherein the zwitterionic compound is administered in conjunction with a conventional antacid.

* * * * *

UNITED STATES PATENT AND TRADEMARK OFFICE
CERTIFICATE OF CORRECTION

PATENT NO. : 4,287,174
DATED : September 1, 1981
INVENTOR(S) : Robert G. Laughlin It is certified that error appears in the above-identified patent and that said Letters Patent are hereby corrected as shown below:

Front Page: Delete "Proct$\underline{o}$r" and insert therefor — Proct$\underline{er}$ —

Col. 5, Ln. 57: Delete "$R - \underset{\underset{R}{|}}{\overset{\overset{R}{|}}{N^+}}$" and insert therefor — $R - \underset{\underset{R}{|}}{\overset{\overset{R}{|}}{M^+}}$ —

Col. 7, Ln. 26: Delete "$\xrightarrow{\underline{heat}}$" and insert therefor — $\xrightarrow{\underline{neat}}$ —

Col. 8, Ln. 8: the word "Representative" should start a new ¶

Col. 8, Ln. 54-55: Delete sentence "hexanoate (51.5g) and sodium iodide (0.30g; Baker)"

Col. 15, Ln. 68: Delete "amount$\underline{s}$" and insert therefor — amount —

Signed and Sealed this

Twenty-fourth Day of November 1981

[SEAL]

Attest:

GERALD J. MOSSINGHOFF

*Attesting Officer*    *Commissioner of Patents and Trademarks*